United States Patent [19]

Irick, Jr. et al.

[11] Patent Number: 5,245,089

[45] Date of Patent: Sep. 14, 1993

[54] ALKYLATION REACTIONS CATALYZED BY GALLIUM-MODIFIED TITANIUM DIOXIDE

[75] Inventors: Gether Irick, Jr., Gray; Leslie S. LaForce, Jonesborough, both of Tenn.

[73] Assignee: Eastman Kodak Company, Rochester, N.Y.

[21] Appl. No.: 965,818

[22] Filed: Oct. 23, 1992

[51] Int. Cl.$^5$ .................... C07C 37/00; C07C 39/06
[52] U.S. Cl. .................... 568/794; 568/650; 568/743; 568/789; 568/790
[58] Field of Search ............... 568/780, 789, 790, 794, 568/743, 744, 650

[56] References Cited

U.S. PATENT DOCUMENTS

| | | | |
|---|---|---|---|
| 3,075,832 | 1/1963 | Ecke et al. | 44/78 |
| 3,093,587 | 6/1963 | Ecke et al. | 252/52 |
| 3,418,379 | 12/1968 | Parsey et al. | 260/624 |
| 3,642,912 | 2/1972 | Sharp et al. | 260/621 R |
| 3,843,606 | 10/1974 | Van Sorge | 260/621 R |
| 4,283,574 | 8/1981 | Leach | 568/804 |
| 4,329,517 | 5/1982 | Taniguchi et al. | 568/804 |

FOREIGN PATENT DOCUMENTS 61-263932 11/1986 Japan.

OTHER PUBLICATIONS

K. Weissermel and H. J. Arpe, "Industrial Organic Chemistry"; English Trans., Verlag Chemie, N.Y., 1978, pp. 293-316.
Wei Mu, J. M. Herrmann and P. Pichat, Catalysis Letters 3 (1989), pp. 73-84.
G. L. Price and Vladislav Kanazirev, J. Mol. Catalysis 66 (1991), pp. 115-120.
J. Kanai and N. Kawata, Applied Catalysis 62 (1990), pp. 140-150.

*Primary Examiner*—Werren B. Lone
*Attorney, Agent, or Firm*—Bernard J. Graves, Jr.; William P. Heath, Jr.

[57] ABSTRACT

Provided is a process for alkylating aromatic compounds in the presence of mixed oxides of titanium and gallium which have been found to be highly active catalysts for the alkylation of aromatics with alkyl esters, alcohols, olefins and ethers. When the alkyl acceptor is a phenol, the catalysts provide high reaction rates and high selectivity for ortho alkylated products.

9 Claims, No Drawings

ALKYLATION REACTIONS CATALYZED BY GALLIUM-MODIFIED TITANIUM DIOXIDE

FIELD OF THE INVENTION

This invention belongs to the field of organic chemistry. More particularly, this invention relates to certain alkylation reactions utilizing gallium modified titanium dioxide.

BACKGROUND OF THE INVENTION

The alkylation of aromatic compounds with olefins and alcohols using acidic zeolites and homogeneous Friedel Crafts catalysts such as aluminum chloride and boron trifluoride is well known. In such cases, the alkylated products tend to be primarily meta and para substituted, with only low concentrations of ortho products. Aluminum and magnesium oxides are commonly used to provide selective ortho substitution [see, for example U.S. Pat. Nos. 3,075,832; 3,093,587; and 3,843,606]; these oxides are generally used as their phenol "esters", e.g. aluminum phenoxide, thereby giving rise to aluminum waste by products.

Alkylation of aromatic compounds is practiced commercially to produce a variety of useful products. For example, benzene is alkylated with ethylene to produce ethylbenzene, an intermediate in the production of styrene (see K. Weissermel and H. J. Arpe, "Industrial Organic Chemistry", English Trans., Verlag Chemie, N.Y., 1978 pp. 293-296). Benzene is also alkylated with propylene to produce cumene, an intermediate for production of phenol (id., pp. 299-300), or to produce 1,3- or 1,4-diisopropylbenzenes, intermediates for production of resorcinol or hydroquinone (pp. 317-318). Phenol is also alkylated with ketones to produce bisphenols such as Bisphenol A (id., p. 315), and with olefins to produce a variety of alkylphenols (id.); alkylation with alcohols, especially methanol, is used to produce cresols and xylenols (id. p. 316), with ortho cresol and 2,6-xylenol being produced with aluminum catalysis (id.). It is thus readily apparent that there is considerable commercial significance to aromatic alkyla tion processes.

U.S. Pat. No. 3,642,912 teaches titanium dioxide as a catalyst for the vapor phase alkylation of phenol with either methanol or ethanol to produe mixtures of alkylated products. In this patent, large amounts of oxygen alkylated products (e.g. methoxybenzene or anisole) as well as meta and para substituted alkyl benzenes were formed; the highest ratio of o cresol to non ortho selective products reported was 3/1, while typical ratios were much lower. The use of olefins, esters and ethers as alkyl donor compounds was not described.

U.S. Pat. No. 3,418,379 teaches gallium oxide as a catalyst for the reaction of phenol with olefins to produce product mixtures in which ortho alkylated products predominate over meta and para isomers. The catalysts were not very active, giving only 26% phenol conversion with 1-butene at 325° C., and 39% conversion at 400° C. after reaction times of 3 hours. The ratio of ortho/para substitution was 22 at 325° C., but dropped to 1.2 at the higher conversion observed at 400° C. More over, the ratio of 2,6 (ortho-ortho) to 2,4 (ortho- para) dibutylphenols produced with butylene and other olefins from C3 to C8 was only 2.1/1, indicating a loss of ortho selectivity at higher levels of alkylation.

U.S. Pat. No. 4,329,517 teaches iron-based catalysts for the vapor phase ortho alkylation of phenols with methanol to produce cresols and xylenols These catalysts contain as a secondary component, a variety of other metals, including gallium; ratios of iron to gallium are typically 54/1. These catalysts gave high selectivity to ortho-substituted products In Wei Mu, J. M. Herrmann and P. Pichat, Catalysis Letters 3(1989) 73-84, titanium tetrachloride containing a gallium salt was burned in a flame to produce a product containing 0.74 atomic % gallium. The surface area of this oxide (50 $m^2/g$) was identical to that of the titanium dioxide prepared in the absence of the gallium, thus indicating that no "chemical mixing" of the oxides had occurred. The absence of "chemical mixing" was also indicated by the fact that in this example, the relative activity of the gallium-doped product for the photooxidation of cyclohexane decreased from 1.0 to 0.24 (ostensibly due to the surface of the titanium dioxide being partially coated with gallium oxide). This reference contains no teaching of such catalysts in alkylation reactions.

Japanese Patent J6 1263932 A 861121 8701; (Derwent 86-01 Wpl 87-003725/01 XRAM-C87-001603) describes compositions consisting of a Group VIII metal (Pt, Ru, Rh, Pd, Os or Ir) on a sulfated titanium dioxide or zirconium oxide which optionally contains a modifying element including aluminum, gallium, indium and thorium. These catalysts were claimed to be useful for xylene isomerizations. Alkylations were not described. In contrast, the catalysts of the present invention do not contain sulfur; we have found that the "chemical mixing" of gallium and titanium gives an active alkylation catalyst and that sulfating is not necessary. Furthermore, a Group VIII metal is not necessary to perform alkylation reactions.

Gallium-containing catalysts having no titanium component are well-known for applications other than alkylation of aromatics For example, gallium has been found to be a useful modifier in zeolites used for the aromatization of alkanes (e.g. ethane-hexane conversion to benzene, toluene and xylenes); this is an upgrading of low-octane fuels to higher octane products. See: G. L. Price and Vladislav Kanazirev, J. Mol Catalysis 66(1991) 115-120; J. Kanai and N. Kawata, Applied Catalysis 62(1990) 141-150, and references cited therein.

Magnesium oxide catalysts containing titanium, uranium or chromium have been claimed as catalysts for the ortho-alkylation of phenols [see U.S. Pat. No. 4,283,574]. The ortho-directing selectivity is consistent with the fact that the catalyst contains magnesium as a major component.

As described below, we have found that insoluble, chemically-mixed oxides of titanium and gallium function as highly active catalysts for the alkylation of aromatic compounds, including phenols. These catalysts provide high levels of ortho substitution and do not produce the undesirable aluminum or magnesium wastes.

SUMMARY OF THE INVENTION

The present invention provides a process for alkylating aromatic compounds in the presence of mixed oxides of titanium and gallium. Such catalysts have been found to be highly active catalysts for the alkylation of aromatics with alkyl donor compounds such as alkyl esters, alcohols, olefins and ethers. When the alkyl acceptor is a phenol, the catalysts provide high reaction rates and high selectivity for ortho alkylated products. A preferred alkyl donor compound is methanol.

DETAILED DESCRIPTION OF THE INVENTION

The present invention provides a process for preparing a compound of Formula (I)

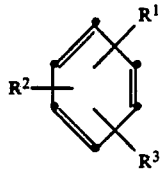 (I)

wherein
$R^1$ and $R^2$ are independently selected from a list consisting of hydrogen; hydroxy; $C_1$-$C_6$ alkoxy; $C_1$-$C_8$ alkyl; and $C_1$-$C_8$ alkyl substituted by one or two groups selected from $C_1$-$C_6$ alkoxy, $C_1$-$C_6$ alkanoyloxy, halo, cyano, and carboxy; and
$R^3$ is $C_1$-$C_{14}$ alkyl, $C_5$-$C_8$ cycloalkyl, or $C_1$-$C_6$ alkyl—O—$C_1$-$C_6$ alkyl;
which comprises
treating a compound of formula (II)

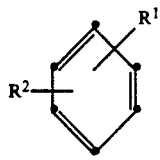

wherein
$R^1$ and $R^2$ are as defined above, with an alkyl donor compound, said alkyl donor compound selected from the group consisting of $R^3$—$OR^4$ ;

wherein
$R^4$ is hydrogen or $C_1$-$C_6$ alkyl;

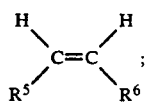

wherein
$R^5$ is hydrogen or $C_1$-$C_6$ alkyl, and wherein
$R^6$ is hydrogen or $C_1$-$C_6$ alkyl, or $R^5$ and $R^6$ are taken together to form a 5 to 8 carbon ring;

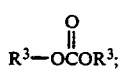

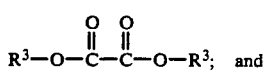 and

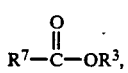

wherein
$R^7$ is $C_1$-$C_6$ alkyl;
in the presence of a gallium-modified titanium dioxide catalyst.

As a preferred embodiment of the present invention, there is provided a process for preparing a compound of the formula

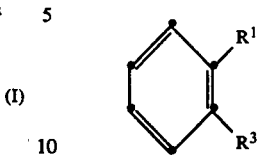

wherein is
$R^1$ is hydroxy; and
$R^3$ is $C_1$-$C_{14}$ alkyl, $C_5$-$C_8$ cycloalkyl, or $C_1$-$C_6$ alkyl—O—$C_1$-$C_6$ alkyl;
which comprises
treating a compound of the formula

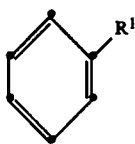

wherein
$R^1$ is as defined above, with an alkyl donor compound, said alkyl donor compound selected from the group consisting of $R^3$—$OR^4$;

wherein
$R^4$ is hydrogen or $C_1$-$C_6$ alkyl;

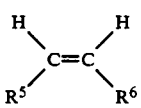

wherein
$R^5$ is hydrogen or $C_1$-$C_6$ alkyl, and wherein
$R^6$ is hydrogen or $C_1$-$C_6$ alkyl, or $R^5$ and $R^6$ are taken together to form a 5 to 8 carbon ring;

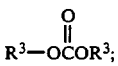

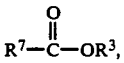 and

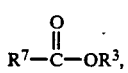

wherein
$R^7$ is $C_1$-$C_6$ alkyl;
in the presence of a gallium modified titanium dioxide catalyst.

The present invention provides a process for the alkylation of aromatic compounds (e.g. phenol, diphenyl ether, hydroquinone, anisole, hydroquinone monomethyl ether, p-cresol, etc) with certain alkyl donor compounds as described above in the presence of a mixed metal oxide of titanium and gallium as catalyst.

Preferred alkyl donor compounds include methanol, methyl acetate, ethyl acetate, dimethyl carbonate, dimethyl oxalate, methyl tert-butyl ether, ethylene, propylene, isobutylene, cyclohexene, cyclohexanol, and the like.

In the above gallium-modified titanium dioxide catalyst, the gallium is preferably present in a weight percent of about 1-33, with a range of 2-14 weight percent being especially preferred. While some effect of the gallium may be seen at atomic % values below 1, the rate of reactions become low. While ratios above 33 will give good rates, the cost of the catalyst becomes prohibitive and much of the gallium will not generally exist as the chemically mixed oxide.

The reaction can be conducted under a variety of conditions which provide for contact of the reactants with the catalyst surface, but preferably are conducted in a fixed-bed reactor in which the catalyst remains stationary and a mixture of the aromatic compound and alkyl donor compound is passed through the catalyst bed as a vapor, liquid, or mixture of vapor and liquid. An inert gas such as nitrogen can optionally be used to assist in moving the reactants and products through the catalyst bed.

Optionally, the reaction can be conducted in a vessel in which the catalyst is slurried in the reaction mixture during the reaction and is removed by filtration prior to isolation of the products.

The process is operable over a broad temperature range, preferably at 60–500° C., depending on the reactants and the type f reactor chosen. For example, the reaction of an olefin and phenol (e.g. isobutylene and phenol) is preferably conducted at a temperature of 60–150° C., while reaction of methanol and phenol would generally require higher temperatures; other alcohols and phenol (e.g. cyclohexanol and phenol) react at lower temperatures, e.g. 120–220° C. Higher temperatures e.g. >200° C. are generally preferred for the efficient alkylation of aromatic compounds with esters.

The modified titanium dioxide catalysts may be prepared by modifying or "chemically mixing" the titanium dioxide with gallium by sintering, i.e., heating a titanium oxide or other metal oxide physical mixture, by precipitating hydrous titania from a monomeric precursor such as titanium tetrachloride or titanium tetraisopropoxide in the presence of a solution containing the gallium element, or by ion exchange of the gallium onto the amorphous or crystalline titania. In this fashion, the titanium dioxide catalyst so modified will be comprised of, for example, a certain amount of Ti—O—Ga bonds. As used herein, the term "chemically mixing" is used in the same sense that it is used in U.S. Pat. No. 5,011,806, incorporated herein by reference.

EXPERIMENTAL SECTION

In this section, the term "BET surface area" will be understood to be the measure of the total surface area of the solids as determined by the adsorption of nitrogen using the method described by W. B. Innes in "Experimental Methods in Catalytic Research", R. B. Anderson, Ed., Academic Press, New York, 1968, pp. 69–77.

EXAMPLE 1

Preparation of 9 Atom % (9.9 wt%) Gallium-Modified Titania

To 500 ml distilled water was added dropwise with stirring 86 g tetraisopropyl titanate. The slurry was stirred 1 hr at 25° C. and filtered. Solids were washed with distilled water, reslurried in ca 100 ml water and refiltered. The solid was added to distilled water and the pH adjusted to 10.0 with ammonium hydroxide. The slurry was heated to 60° C., stirred for 3 hrs., cooled to 25° C. and filtered. The white solid was then added to a solution of 14.23 g gallium nitrate in 200 ml water and the resulting slurry was heated to 60° C. and stirred for 3 hours. Upon cooling to 25° C., solids were removed by filtration, washed once with distilled water and dried on a steam bath. Calcination by heating at 200° C. for 1 hour, 350° C. for 1 hour and 450° C. for 3 hours gave the mixed metal oxide, BET surface area 141 m2/g.

EXAMPLE 2

Preparation of 1.4 Atom % Gallium-Modified Titania

To 700 ml distilled water was added in 15 min. with stirring 172g (0.61 mole) titanium tetraisopropoxide. The slurry was stirred for 1 hour, filtered, washed by reslurrying in 500 ml water and refiltering. Solid was then mixed with 320 ml water, pH adjusted to 10 with ammonium hydroxide and the mixture heated to 60° C. and stirred for 3 hours. Cooled to 25° C., filtered and washed once with 50 ml water. The white solid was then added with stirring to a solution of 3.56g (0.0086 mole) gallium nitrate nonahydrate in 500 ml distilled water. The slurry was then heated to 60° C. and stirred for 3 hrs. Cooled to 25° C., filtered, washed with 50 ml water and dried on a steam bath. Calcined in air at 500 ml/min flow rate by heating slowly to 200° C., holding 1 hr., then 1 hr at 350° C., followed by 3 hrs at 550° C. White solid.

EXAMPLE 3

Preparation of 5.3 Atom % Gallium-Modified Titania

The procedure of Example 2 was repeated, but using 14.23 g gallium nitrate nonahydrate.

EXAMPLE 4

Preparation of 15.3 Atom % Gallium-Modified Titania

The procedure of Example 2 was repeated, but using 46.92 g gallium nitrate nonahydrate.

EXAMPLE 5

Alkylation of Phenol with Methyl Benzoate

A 2/1 mole/mole mixture of phenol and methyl benzoate was fed at 425° C. at a rate of 5 ml/hr to the top of a fixed bed reactor containing 5 g of the catalyst of Example 1. Conversions of phenol and methyl benzoate were 56 and 48% respectively. Phenol derived products consisted of the following (mole % concentrations noted).

| Anisole | 8.3 |
| o-Cresol | 65.0 |
| p-Cresol | 9.3 |
| 2,4-Dimethylphenol | 8.2 |
| 2,6-Dimethylphenol | 8.2 |

EXAMPLE 6

Alkylation of Phenol with Methyl Acetate

A 2/1 mole/mole mixture of phenol and methyl acetate was reacted as in Example 5 at 425° C., giving 52% conversion of the phenol. Phenol derived products consisted of the following (mole% concentrations noted).

| | | |
|---|---|---|
| Anisole | 4.9 | |
| o-Cresol | 73.0 | |
| p-Cresol | 4.9 | |
| 2,4-Dimethylphenol | 4.3 | |
| 2,6-Dimethylphenol | 12.9 | |

EXAMPLE 7

Alkylation of Phenol with Methanol

A 2/1 mole/mole mixture of phenol and methanol was reacted as in Example 5 at temperatures of 425° C., 325° C. and 250° C., giving 64, 44 and 27% phenol conversions respectively. Phenol-derived products consisted of the following (mole% concentrations noted).

| | 425° C. | 325° C. | 250° C. |
|---|---|---|---|
| Anisole | 2.3 | 16.6 | 76.9 |
| o-Cresol | 65.9 | 58.0 | 23.1 |
| p-Cresol | 7.0 | — | — |
| 2,4-Dimethylphenol | 6.2 | 4.1 | — |
| 2,6-Dimethylphenol | 16.6 | 7.3 | — |
| 3-Ethylphenol | — | 7.3 | — |
| 2,3,6-Trimethylphenol | 1.8 | 3.3 | — |
| 3,4,5-Trimethylphenol | — | 3.3 | — |

We claim:

1. A process for preparing a compound of the formula

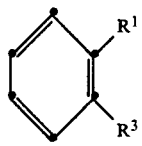

wherein is
 $R^1$ is hydroxy; and
 $R^3$ is $C_1$-$C_6$ alkyl, $C_5$-$C_8$ cycloalkyl, or $C_1$-$C_6$ alkyl—O—$C_1$-$C_6$ alkyl;
which comprises
 treating a compound of the formula

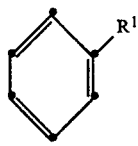

wherein
 $R^1$ is as defined above, with an alkyl donor compound, said alkyl donor compound selected from the group consisting of $R^3$—$OR^4$;

wherein
 $R^4$ is hydrogen or $C_1$-$C_6$ alkyl;

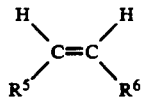

wherein
 $R^5$ is hydrogen or $C_1$-$C_6$ alkyl, and wherein
 $R^6$ is hydrogen or $C_1$-$C_6$ alkyl, or $R^5$ and $R^6$ are taken together to form a 5 to 8 carbon ring;

$$R^3-\overset{O}{\underset{\|}{O}}CR^3;$$

$$R^3-O-\overset{O}{\underset{\|}{C}}-\overset{O}{\underset{\|}{C}}-O-R^3; \text{ and}$$

$$R^7-\overset{O}{\underset{\|}{C}}-OR^3,$$

wherein
 $R^7$ is $C_1$-$C_6$ alkyl;
in the presence of a gallium modified titanium dioxide catalyst.

2. The process of claim 1, wherein the alkyl donor compound is a compound of the formula $R^3$—$OR^4$.

3. The process of claim 1, wherein the compound of the formula $R^3$—$OR^4$ is selected from the list consisting of methanol, ethanol, n-propanol, cyclohexanol, t-butyl methyl ether, dimethyl ether, and diethyl ether.

4. The process of claim 1, wherein the alkyl donor compound is methanol.

5. The process of claim 1, wherein the alkyl donor compound is a compound of the formula

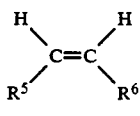

wherein
 $R^5$ is hydrogen or $C_1$-$C_6$ alkyl, and wherein
 $R^6$ is hydrogen or $C_1$-$C_6$ alkyl, or $R^5$ and $R^6$ are taken together to form a 5 to 8 carbon ring.

6. The process of claim 1, wherein $R^5$ is hydrogen.

7. The process of claim 1, wherein $R^6$ is hydrogen.

8. The process of claim 1, wherein $R^5$ and $R^6$ are taken together to form a 5 to 8 carbon ring.

9. The process of claim 1, wherein the alkyl donor compound is selected from the group consisting of ethylene, propylene, butylene, and cyclohexene.

* * * * *